United States Patent
Machida

(10) Patent No.: US 10,143,509 B2
(45) Date of Patent: Dec. 4, 2018

(54) MEDICAL SCREW

(71) Applicant: TAMA MEDICAL CO. LTD., Tokyo (JP)

(72) Inventor: Eiichi Machida, Tokyo (JP)

(73) Assignee: TAMA MEDICAL CO. LTD., Tokyo (JP)

( * ) Notice: Subject to any disclaimer, the term of this patent is extended or adjusted under 35 U.S.C. 154(b) by 181 days.

(21) Appl. No.: 14/904,103

(22) PCT Filed: Jul. 11, 2014

(86) PCT No.: PCT/JP2014/068613
§ 371 (c)(1),
(2) Date: Jan. 10, 2016

(87) PCT Pub. No.: WO2015/005482
PCT Pub. Date: Jan. 15, 2015

(65) Prior Publication Data
US 2016/0151101 A1 Jun. 2, 2016

(30) Foreign Application Priority Data

Jul. 12, 2013 (JP) ................................. 2013-146779

(51) Int. Cl.
*A61B 17/86* (2006.01)
*A61B 17/88* (2006.01)

(52) U.S. Cl.
CPC ........ *A61B 17/8891* (2013.01); *A61B 17/862* (2013.01); *A61B 17/864* (2013.01);
(Continued)

(58) Field of Classification Search
CPC . A61B 17/8891; A61B 17/8615; A61B 17/84; A61B 17/7082
See application file for complete search history.

(56) References Cited

U.S. PATENT DOCUMENTS 4,987,892 A * 1/1991 Krag .................. A61B 17/7037
606/264
5,019,079 A * 5/1991 Ross .................... A61B 17/863
411/389

(Continued)

FOREIGN PATENT DOCUMENTS

CN 101827560 A 9/2010
JP 2011500215 A 1/2011
(Continued)

OTHER PUBLICATIONS

International Search Report dated Nov. 14, 2014.

*Primary Examiner* — Christian Sevilla
(74) *Attorney, Agent, or Firm* — Li & Cai Intellectual Property (USA) Office

(57) ABSTRACT

The outer periphery of a head section (11e) of a medical screw (11) is provided with an inverse external screw thread (11h) that is formed in the opposite screw direction from that of a screw thread (11b) provided to a tip section (11a). An inverse internal screw thread (14a) provided to the leading end of a rod-shaped body constituting an extraction jig (14) is rotated in the opposite direction from the screw direction of the screw thread (11b) so as to be screwed onto the inverse external screw thread (11h) and thereby integrate the screw (11) and the extraction jig (14). The screw (11) is gently extracted from the bone fracture site (D) and is removed from the body by rotating the extraction jig in the reverse direction from the insertion direction of the screw (11).

8 Claims, 9 Drawing Sheets

(52) U.S. Cl.
CPC ...... *A61B 17/8615* (2013.01); *A61B 17/8883* (2013.01); *A61B 17/8888* (2013.01)

(56) References Cited

U.S. PATENT DOCUMENTS

| | | | | |
|---|---|---|---|---|
| 5,100,405 A * | 3/1992 | McLaren | ............... | A61B 17/72 606/304 |
| 5,498,265 A * | 3/1996 | Asnis | ............... | A61B 17/74 606/315 |
| 5,586,984 A * | 12/1996 | Errico | ............... | A61B 17/7037 606/264 |
| 5,667,508 A * | 9/1997 | Errico | ............... | A61B 17/7032 606/301 |
| 5,964,760 A * | 10/1999 | Richelsoph | ........ | A61B 17/7037 606/278 |
| 5,976,139 A * | 11/1999 | Bramlet | ............. | A61B 17/1659 606/282 |
| 6,030,162 A * | 2/2000 | Huebner | ............ | A61B 17/1682 411/263 |
| 6,053,916 A * | 4/2000 | Moore | ................ | A61F 2/30988 606/86 R |
| 8,764,764 B2 * | 7/2014 | Dahners | ............. | A61B 17/8047 606/104 |
| 2007/0016200 A1* | 1/2007 | Jackson | ............. | A61B 17/7005 623/17.16 |
| 2010/0152740 A1 | 6/2010 | O'Reilly et al. | | |
| 2012/0197311 A1 | 8/2012 | Kirschman | | |

FOREIGN PATENT DOCUMENTS

| | | |
|---|---|---|
| JP | H 10272142 A | 1/2011 |
| WO | WO 2009/052294 A1 | 4/2009 |
| WO | WO 2013/134004 A1 | 9/2013 |

* cited by examiner

[Fig. 1]
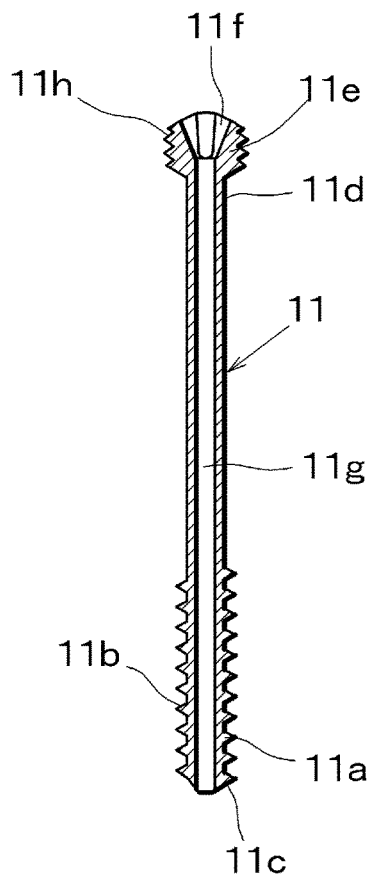
[Fig. 2]
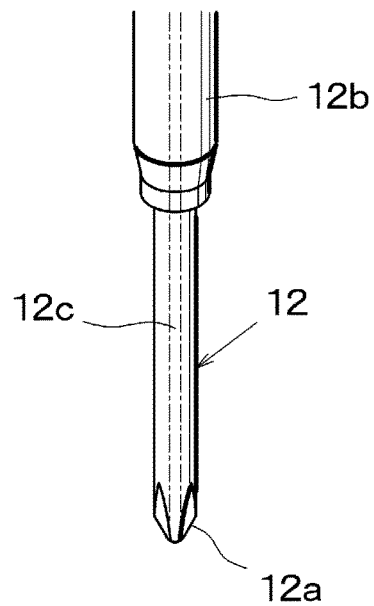

[Fig. 3]
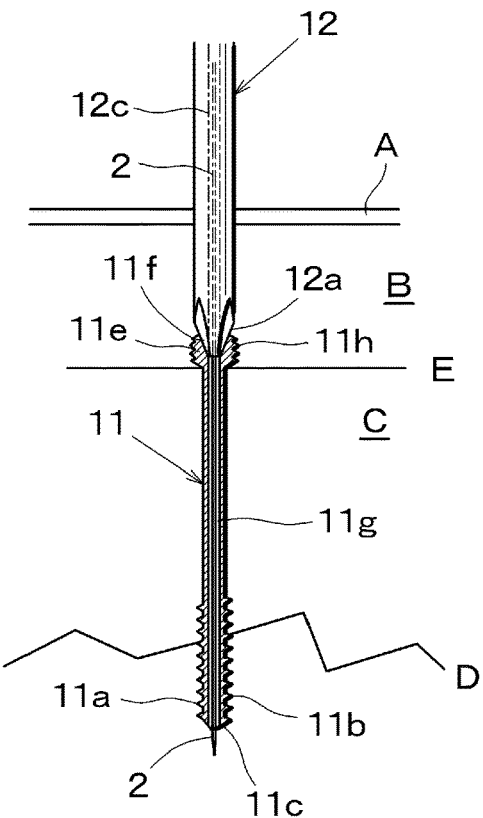
[Fig. 4]
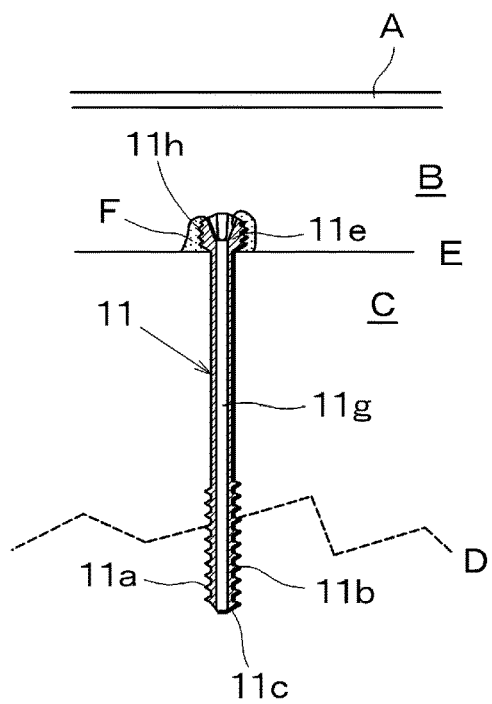

[Fig. 5]
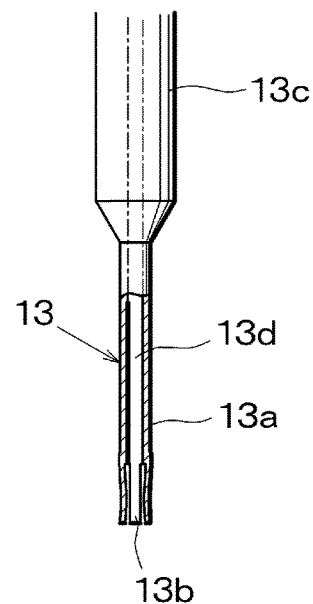
[Fig. 6]
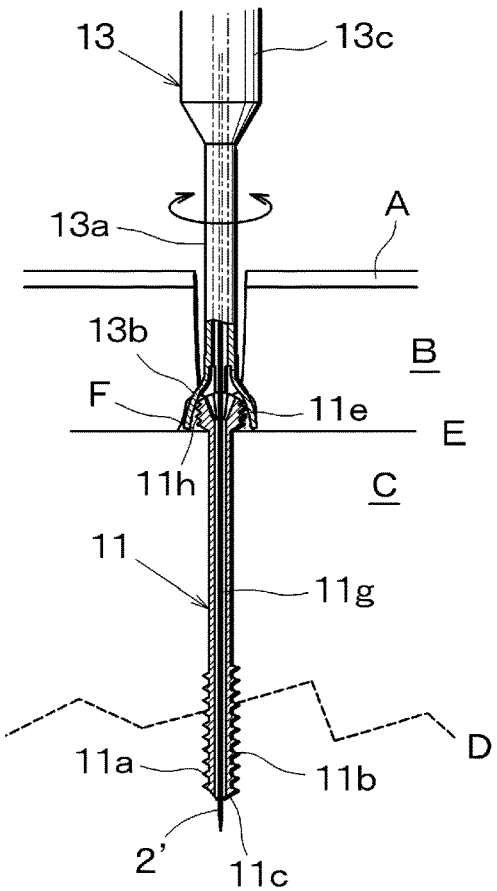

[Fig. 7]
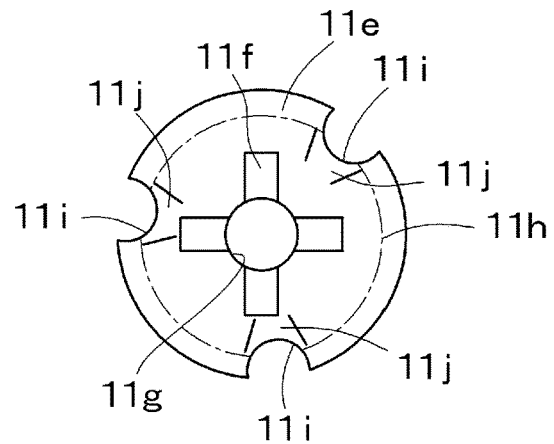
[Fig. 8]
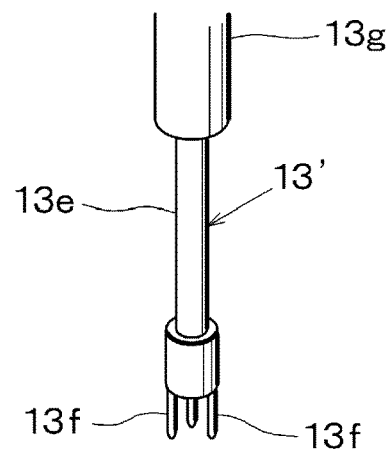
[Fig. 9]
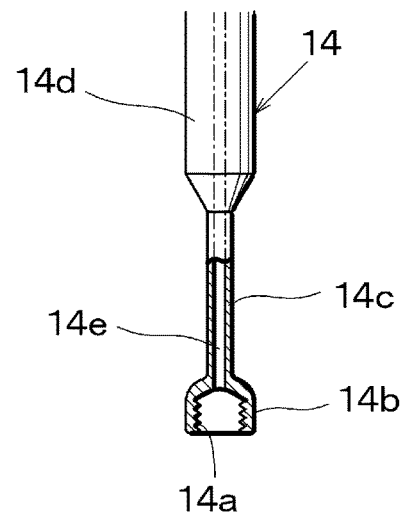

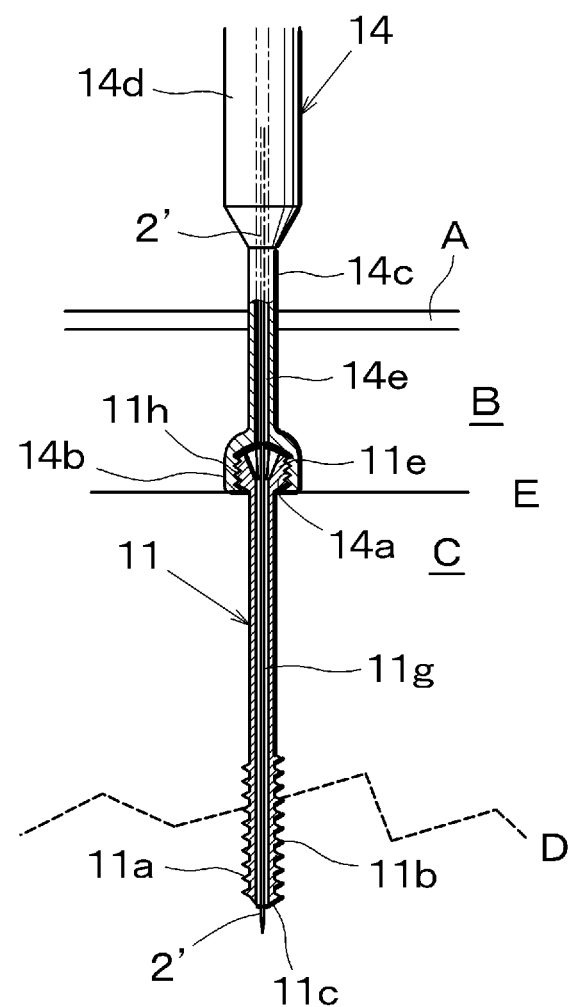
[Fig. 10]

[Fig. 11]
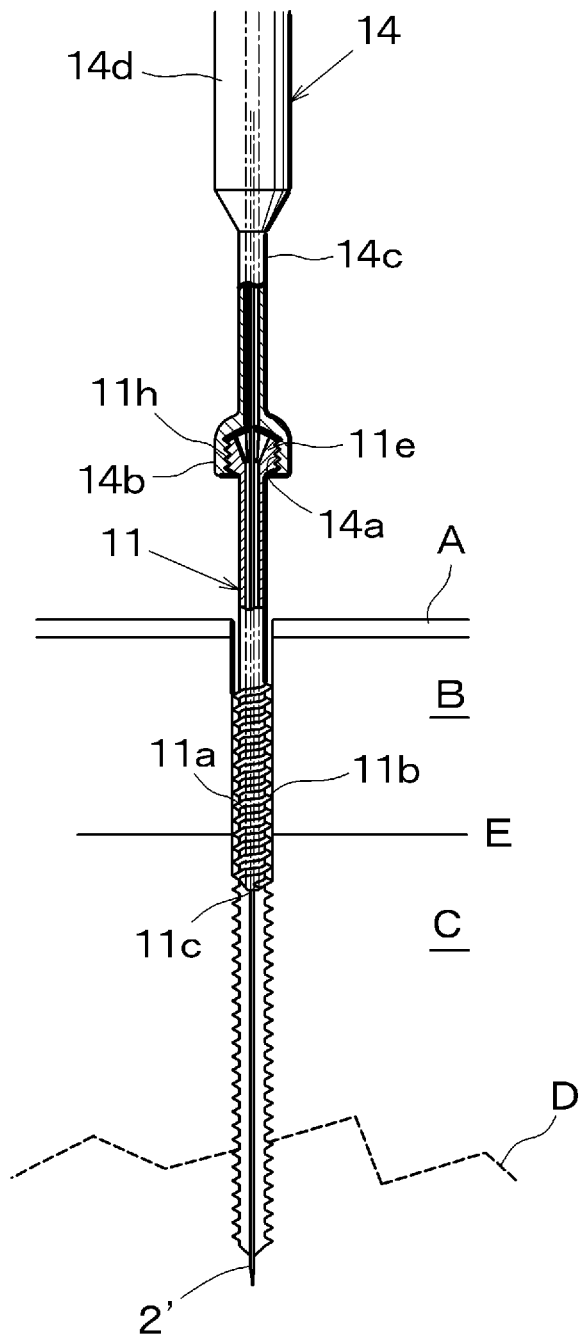

[Fig. 12]
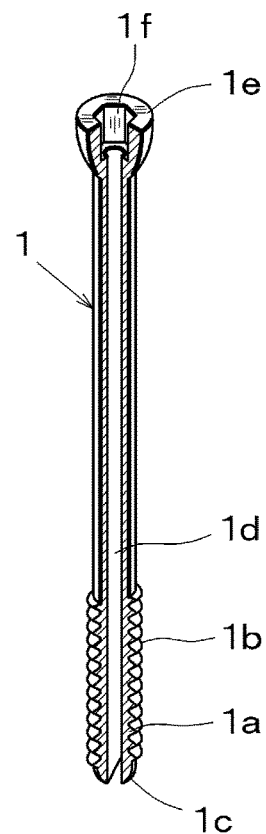
[Fig. 13]
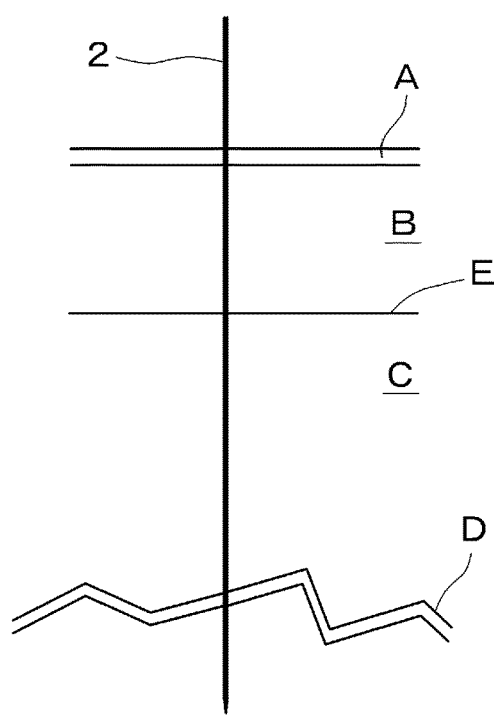

[Fig. 14]
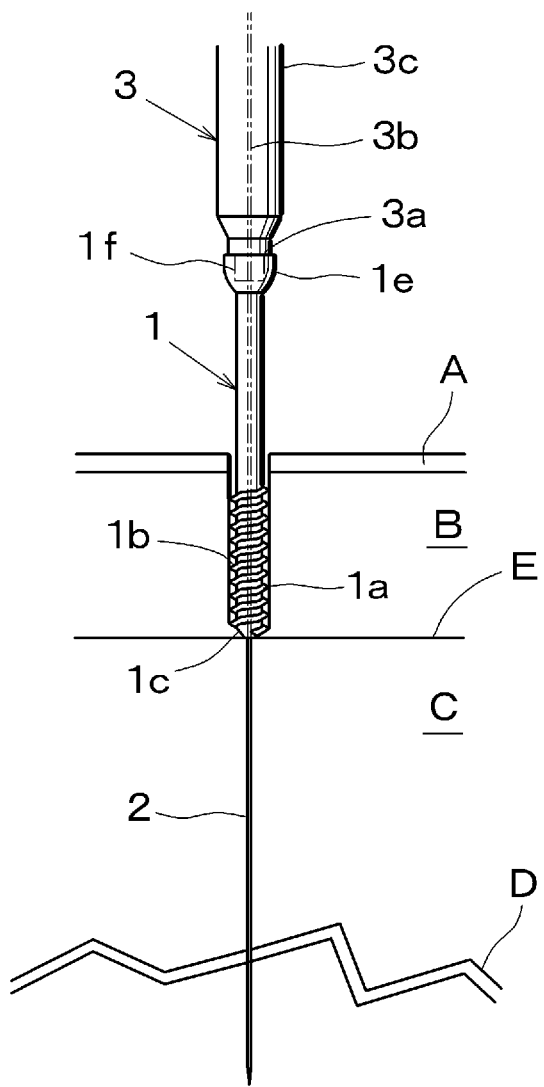

[Fig. 15]
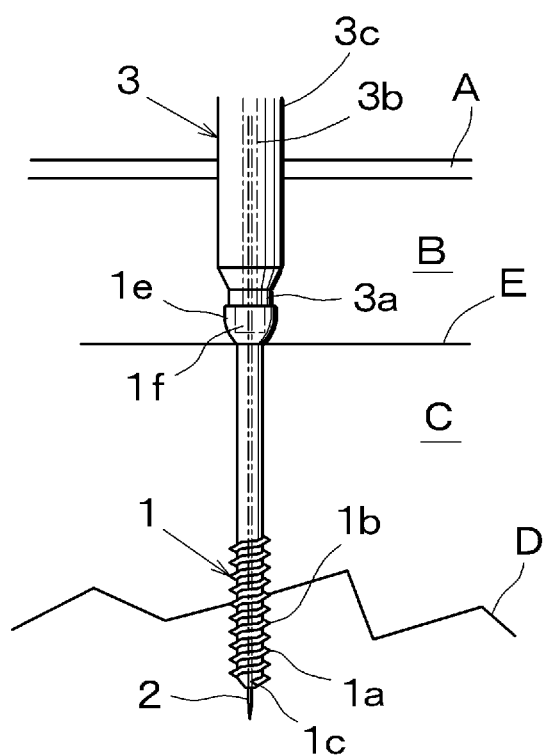

MEDICAL SCREW

TECHNICAL FIELD

The present invention relates to a medical screw for joining a fracture site and a withdrawal operating jig for a medical screw.

BACKGROUND ART

PTL 1 discloses a medical screw 1 having a hollow hole, which is referred to as a cannulated screw as illustrated in FIG. 12. The screw 1 is used for joining a fracture site in a medical field in the related art, is provided with a screw thread portion 1b formed on an outer surface of a distal end portion 1a, is provided with a drill blade 1c formed at an extremity thereof, and is provided with a through hole 1d extending along a center axis along an entire length thereof. A rotational operating portion if formed of, for example, a hexagonal depression is provided at an entry of the through hole 1d of a head portion 1e of the screw 1, and the fracture site is joined by screwing the screw thread portion 1b into a bone by fitting a distal end portion of a driver-type rotational operation jig into the rotational operating portion if and rotating the same.

A procedure of screwing the screw 1 of the related art into the bone starts with piercing a metallic guide pin 2 through an incised skin A and a subcutaneous structure B in a fracture site D of a bone C substantially orthogonal to the fracture site D under anesthesia as illustrated in FIG. 13. A distal end of the guide pin 2 is pointed like a drill, is pieced through the skin A and the subcutaneous structure B as is, and is screwed into the bone C by being rotated by a motor or the like when the distal end comes into abutment with a bone cortex surface E of the bone C.

Subsequently, an upper end of the guide pin 2 is inserted into the through hole 1d on the distal end portion 1a side of the screw 1, and the screw 1 is pushed inward while being guided along the guide pin 2. The upper end of the guide pin 2 projected further upward from the head portion 1e of the screw 1 is inserted into a through hole 3b of a rotational operation jig 3. Subsequently, as illustrated in FIG. 14, the screw 1 is pushed inward of the skin A and the subcutaneous structure B by the rotational operation jig 3, and is rotated clockwise by a manual operation using a grip portion 3c of the rotational operation jig 3 after the distal end portion 1a of the screw 1 has come into abutment with the bone cortex surface E. With a rotation of the screw 1, the screw thread portion 1b is screwed into an interior of the bone C along the guide pin 2 while drilling the bone C with the drill blade 1c provided at the distal end thereof. The screw 1 may be screwed by the rotational operation jig 3 such as a medical electric drill or the like.

By screwing the screw 1 into the bone C while observing an X-ray TV monitor with radioscopy, the screw thread portion 1b penetrates through the fracture site D and starts unification. Then, as illustrated in FIG. 15, when the head portion 1e of the screw 1 reaches the bone cortex surface E, fixation of the fracture site D by the screw 1 is achieved.

The rotational operation jig 3 is pulled out from the guide pin 2, and finally, the guide pin 2 is withdrawn from the bone C, and then the skin A or the like is sutured, whereby a joining process on the fracture site D with the screw 1 is completed.

Since the fracture site D is united after an elapse of several months from the joining process, a process of withdrawing the screw 1 which has completed its role is performed. After the skin A and the subcutaneous structure B have incised, the screw 1 is taken out from the bone C by loosening the screw thread portion 1b, which is screwed in, by fitting a distal end portion 3a of the rotational operation jig 3 into the rotational operating portion if of the screw 1 and rotating the same counterclockwise. In this case, a withdrawal guide pin is preferably inserted into the screw 1 to guide the rotational operation jig 3 to the head portion 1e of the screw 1.

At a time when the fracture site D is unified by the fixation of the screw 1, callus is generated newly around the head portion 1e of the screw 1 in many cases, so that the head portion 1e of the screw 1 may be buried in the callus. In this case, since the callus becomes an obstacle which makes the rotational operation jig 3 difficult to fit into the rotational operating portion if of the screw 1, the callus needs to be removed.

The screw thread portion 1b of the screw 1 is pulled out from the bone C by rotating the rotational operation jig 3 counterclockwise after the rotational operation jig 3 is fitted correctly into the rotational operating portion 1f. At the time of being pulled out, the screw 1 is moved upward by a reaction force of the bone C until the screw thread portion 1b screwed into the bone C reaches the bone cortex surface E. However, in the case where the screw 1 is still buried in the subcutaneous structure B, the screw thread portion 1b runs idle and thus puling out of the screw 1 becomes difficult.

In the case where the screw 1 comes off the bone C when screwing the screw 1 at the time of joining the fracture site D and thus is screwed into the subcutaneous structure B as well, the screw 1 needs to be pulled out once to retry screwing. At this time, even though the screw 1 is rotated counterclockwise, the screw thread portion 1b runs idle and thus the screw 1 cannot be pulled out.

Furthermore, if several months have been elapsed from the joining process, the bone C having the screw 1 screwed therein may reject the metal, and thus a gap may be formed between the bone C and the screw 1. In such a case as well, the screw thread portion 1b runs idle and thus cannot be pulled out easily even though the screw 1 is rotated.

PTL 2 discloses an orthopedic screw having the same function as the medical screw 1, and describes that a reverse internal thread portion having a thread in a reverse direction to a direction of the screw thread formed at the distal end portion, is formed inside a head portion of the orthopedic screw, and the screw is pulled out by engaging an operating jig with the reverse internal thread portion and rotating the screw in a reverse thread direction.

The screw can be pulled out easily by using this orthopedic screw, because a withdrawal operating jig is integrated with the orthopedic screw via the reverse internal thread portion and the screw thread can be loosened from the bone by rotating the operating jig in the reverse direction.

CITATION LIST

Patent Literatures

PTL 1: JP-A-10-272142
PTL 2: JP-T-2011-500215

SUMMARY OF THE INVENTION

Technical Problem

However, the reverse internal thread portion of the orthopedic screw disclosed in PTL 2 is formed inside the head portion of the screw. Therefore, if a foreign substance, for example, callus, is adhered to inside of the head portion, the reverse internal thread portion has a disadvantage of becoming incapable of functioning unless the foreign substance is removed. Removal of the foreign substance is very troublesome, and proper engagement of the operating jig with the reverse thread portion cannot be achieved as long as the foreign substance remains in the head portion. Therefore, the foreign substance needs to be completely taken out from the head portion, and this is a big problem in the surgical operation which needs to be quick.

It is a first object of the invention to solve the above-described problem and provide a medical screw which can be withdrawn easily and quickly from inside the bone by using a reverse external thread portion formed on an outer periphery of a head portion after the bone has unified or at the time of replacement.

It is a second object of the invention to provide a withdrawal operating jig for a medical screw configured to achieve a withdrawal of the medical screw described above reliably, easily, and quickly.

Solution to Problem

A medical screw according to the invention for achieving the above described objects is a medical screw formed of a metallic material for joining a fracture site and including: a screw thread portion formed on an outer surface of a distal end portion; and an external thread portion formed on an outer periphery of a head portion which is provided at a rear end portion and whose top portion bulges in an arcuate shape, in which the external thread portion is formed in a reverse direction to a direction of a thread of the screw thread portion.

A withdrawal operating jig for a medical screw according to the invention is a withdrawal operating jig for withdrawing a medical screw from a fracture site, the medical screw including: a screw thread portion formed on an outer surface of a distal end portion; and an external thread portion formed on an outer periphery of a head portion provided at a rear end portion and swelled in an arcuate shape at a top portion thereof, in which the external thread portion provided on the head portion being formed of a metallic material so as to have a thread formed in a reverse direction to a direction of a thread of the screw thread portion, including an engaging portion formed into an internal thread portion configured to engage the external thread portion provided on the outer periphery of the head portion of the medical screw at a front end portion of a rod-shaped member.

BRIEF DESCRIPTION OF DRAWINGS

FIG. 1 is a cross-sectional view of a medical screw of an embodiment.
FIG. 2 is a perspective view of a screwing-in operating jig.
FIG. 3 is an explanatory drawing illustrating a state in which the medical screw is screwed into a fracture site.
FIG. 4 is an explanatory drawing illustrating a state in which callus is formed in the vicinity of a head portion.
FIG. 5 is a cross-sectional view illustrating a principal portion of a callus separation operating jig.
FIG. 6 is an explanatory drawing illustrating a removal of the callus by the callus separation operating jig.
FIG. 7 is an enlarged plan view illustrating a modification of the head portion of the medical screw.
FIG. 8 is a perspective view of another callus separation operating jig.
FIG. 9 is a cross-sectional view of a principal portion of a withdrawal operating jig.
FIG. 10 is an explanatory drawing illustrating a state of inserting the withdrawal operating jig.
FIG. 11 is an explanatory drawing illustrating a state of withdrawing the medical screw from inside a bone.
FIG. 12 is a perspective cross-sectional view of a medical screw of the related art.
FIG. 13 is an explanatory drawing in a state in which a guide pin is inserted into the fracture site.
FIG. 14 is an explanatory drawing of a state in which the medical screw of the related art is inserted into a subcutaneous structure.
FIG. 15 is an explanatory drawing illustrating a state in which the medical screw of the related art is screwed into the fracture site.

DESCRIPTION OF EMBODIMENTS

The invention will be described in detail with reference to embodiments illustrated in FIG. 1 to FIG. 11.

FIG. 1 is a cross-sectional view of a medical screw 11 of an embodiment. A distal end portion 11a of the tube-shaped screw 11 formed of a metallic material such as titanium is provided with a screw thread portion 11b, which is a right-handed thread, formed on an outer surface thereof and is provided with a drill blade 11c at an extremity thereof. The screw thread portion 11b may be provided not only on the distal end portion 11a, but also on the outer surface entirely in a longitudinal direction of the screw 11.

A rear end portion 11d is provided with a head portion 11e at a distal end thereof, and is provided with a rotational operating portion 11f formed into, for example, a cross-shaped plus groove configured to fit in a distal end portion of a screwing-in operating jig, which will be described later, at a center portion of a top surface of the head portion 11e. A through hole 11g having a predetermined diameter is provided along a center axis from the distal end portion 11a to the head portion 11e of the screw 11, and the through hole 11g is configured to allow insertion of a guide pin and a withdrawal guide pin, which have been described in conjunction with the related art.

The through hole 11g has a substantially circular shape in cross section, has the same diameter from the distal end portion of the screw 11 to a rear end portion thereof, and has an inner diameter on the order of 2 mm. The head portion 11e is provided with a reverse external thread portion 11h on an outer periphery thereof as a left-handed thread in a reverse direction to a direction of the screw thread portion 11b.

The shape of the top portion of the head portion 11e is preferably swelled upward, for example, in an arcuate shape, so that a callus separation operating jig and a withdrawal operating jig, which will be described later, can be easily guided to the reverse external thread portion 11h.

The entire length of the screw 11 is, for example, on the order of 30 to 60 mm. However, it is desired to provide a plurality of types having different lengths and thicknesses and select one suitable for the size of a fracture site and the position of the fracture site such as a finger bone or a femur as needed. However, the screws 11 in all sizes preferably have the head portions 11e having the same outer diameter in order to be used commonly for the callus separation operating jig and the withdrawal operating jig, which will be described later.

FIG. 2 is a perspective view of a screwing-in operating jig 12, which is provided with a plus portion projecting from a distal end portion 12a thereof and being configured to fit the rotational operating portion 11f of the screw 11, and a through hole 12c having a circular shape in cross section extending from the distal end portion 12a to a grip portion 12b at a rear end. The inner diameter of the through hole 12c substantially matches the inner diameter of the through hole 11g of the screw 11, and is configured to allow insertion of the guide pin therein.

When screwing the screw 11 into a bone C, a skin A or the like is incised, and then a guide pin 2 inserted into the bone C is inserted through the through hole 11g of the screw 11 and the through hole 12c of the screwing-in operating jig 12, and the distal end portion 12a of the screwing-in operating jig 12 is fitted into the rotational operating portion 11f of the screw 11 while being guided by the guide pin 2 as illustrated in FIG. 3. Then, by rotating the screwing-in operating jig 12 clockwise in a direction of the right-handed thread by a manual operation or electrically, the drill blade 11c of the screw 11 drills the bone C to cause the screw thread portion 11b to be screwed into the bone C. Then, by continuing screwing until the head portion 11e reaches a bone cortex surface E, a fracture site D is joined. Subsequently, the screwing-in operating jig 12 and the guide pin 2 are pulled out and the skin A and the like is sutured, so that the joint with the screw 11 is completed.

By forming the shape of the depressed-shaped rotational operating portion 11f of the screw 11 into a depressed plus groove as illustrated in FIG. 1, the distal end portion 12a of the screwing-in operating jig 12 can be fitted to the rotational operating portion 11f of the screw 11 and rotated even though the size of the plus shape of the distal end portion 12a of the screwing-in operating jig 12 is different to some extent.

The shape of the distal end portion 12a of the screwing-in operating jig 12 may be formed into a minus shape, and in this case, the shape of the rotational operating portion 11f of the screw 11 needs only to be a depressed linear shape or a cross shape, and the rotational operating portion 11f can be rotated even though the size is different to some extent from the minus shape of the distal end portion 12a. Alternatively, the shape of the depressed-shaped rotational operating portion 11f may be a shape which allows fitting of the rotational operation jig 3 having a polygonal shape such as a hexagonal shape as described in the description of the related art without problem. However, in this case, the screw 11 cannot be rotated unless the screwing-in operating jig 12 has the distal end portion 12a having a shape which completely fits.

In the case where the fracture site D is unified after an elapse of several months and thus the screw 11 which is no longer necessary is taken out, the skin A needs to be incised to allow the callus separation operating jig, the withdrawal operating jig, which will be described later, and the screw 11 to pass through a subcutaneous structure B and the skin A. However, since the skin A and the subcutaneous structure B extend to some extent, an incision of the skin A and the subcutaneous structure B on the order of 4 mm in outer diameter above the head portion 11e is sufficient.

In the vicinity of the head portion 11e of the screw 11, callus F is formed with an elapse of time as illustrated in FIG. 4, so that the head portion 11e may be buried in the callus F. In this case, in order to remove the callus F in the periphery of the head portion 11e, a callus separation operating jig 13 as illustrated in FIG. 5 is used as needed. The callus separation operating jig 13 is a screw driver-type jig provided with a plurality of tongue-shaped blade portions 13b having an elasticity arranged in an annular shape at a distal end of a shaft portion 13a, and is configured to have an insertion hole 13d from a distal end thereof to a grip portion 13c so as to allow insertion of the withdrawal guide pin.

As illustrated in FIG. 6, a withdrawal guide pin 2' is pierced into the bone C, the withdrawal guide pin 2' is inserted into the through hole 11g of the screw 11, and the callus separation operating jig 13 is pushed therein along the withdrawal guide pin 2'. Subsequently, the blade portion 13b is rotated by the grip portion 13c to remove the callus F in the periphery of the head portion 11e to completely expose the reverse external thread portion 11h provided in the outer periphery of the head portion 11e. In the case where the blade portion 13b of the callus separation operating jig 13 is inserted so as to extend along the surface of the head portion 11e, the callus F can be separated easily. By separating and removing the callus F in the periphery of the head portion 11e, engagement of the withdrawal operating jig, which will be described later, with the reverse external thread portion 11h of the head portion 11e is enabled.

FIG. 7 is an enlarged plan view of a head portion 11e of a medical screw 11 of a modification. A plurality, three for example, of groove portions 11i for separating the callus are formed on the periphery of the head portion 11e of the screw 11 from the top portion to the side in a direction orthogonal to a peripheral direction, and depressed guide portions 11j are provided at positions from the top portion to the groove portions 11i.

When a pin or the like is inserted from above the groove portions 11i covered with the callus F via the guide portions 11j and opened forcedly, the fragile callus F adhered to the periphery of the head portion 11e can be separated easily, so that the reverse external thread portion 11h can be exposed. The presence of the groove portions 11i does not affect engagement of the reverse external thread portion 11h.

It is also possible to use a callus separation operating jig 13' as illustrated in FIG. 8 to cause the groove portions 11i to operate. In other words, the callus separation operating jig 13' has, for example, resiliency at a distal end of a rod body portion 13e, and is provided with three metallic pins 13f arranged at positions matching the groove portion 11i of the head portion 11e of the screw 11. An insertion hole, which is not illustrated, for allowing insertion of the withdrawal guide pin 2' is provided at a center portion from the distal end of the rod body portion 13e to a grip portion 13g.

When removing the callus F formed on the outer periphery of the screw 11, the callus F can be pushed outward and separated easily by a resilient force of the metallic pins 13f only by inserting the metallic pins 13f of the callus separation operating jig 13' into the groove portions 11i via the push-in guide portion 11j along the arcuate-shaped swelling of the head portion 11e.

FIG. 9 is a cross-sectional view of a principal portion of a withdrawal operating jig 14. The withdrawal operating jig 14 includes a cap nut portion 14b having a reverse internal thread portion 14a on an inner side thereof as an engaging portion at a front end portion of the rod-shaped member, and the reverse internal thread portion 14a is configured to engage the reverse external thread portion 11h of the screw 11. An insertion hole 14e for allowing the withdrawal guide pin 2' to be inserted therethrough is formed at center portions of a shaft portion 14c and a grip portion 14d of the withdrawal operating jig 14.

As illustrated in FIG. 10, the skin A or the like is incised and an upper end of the withdrawal guide pin 2' pierced into the bone C is inserted into the insertion hole 14e of the withdrawal operating jig 14. By moving the withdrawal operating jig 14 downward along the withdrawal guide pin 2', the reverse internal thread portion 14a of the withdrawal operating jig 14 is guided to the head portion 11e of the screw 11 and brought into abutment with the reverse external thread portion 11h. In this case, by using the withdrawal guide pin 2' as the withdrawal operating jig 14, and forming the top portion of the head portion 11e into an arcuate shape, the reverse internal thread portion 14a is guided correctly to the reverse external thread portion 11h.

Subsequently, the withdrawal operating jig 14 is rotated counterclockwise, that is, in a reverse thread direction by the grip portion 14d, the reverse internal thread portion 14a of the withdrawal operating jig 14 is sufficiently screwed into the reverse external thread portion 11h of the screw 11, and the withdrawal operating jig 14 is unified with the screw 11.

When the withdrawal operating jig 14 is further rotated counterclockwise subsequently to the unification, the screw 11 can be taken out by loosening the screw thread portion 11b of the screw 11 with respect to the bone C as illustrated in FIG. 11. Even though the screw 11 is withdrawn out from the bone C and runs idle, since the screw 11 is integrated with the withdrawal operating jig 14, the screw 11 can be pulled out of the body by puling the withdrawal operating jig 14 upward as is. Finally, the withdrawal guide pin 2' is withdrawn and the skin A or the like is sutured, whereby the screw 11 is completely taken out.

After the screw 11 has pulled out, there remains a void in the bone C. However, the void is filled up by the bone C with an elapse of time.

In the description of the embodiment given above, the screw thread portion 11b of the screw 11 is the right-handed thread and the reverse external thread portion 11h is the left-handed thread. However, this relationship may be vice versa.

Although the guide pin 2 and the withdrawal guide pin 2' are described as separate members, these members may be the same member, and these are not an absolutely imperative member. When the guide pin 2 and the withdrawal guide pin 2' are not used, the through hole 11g of the screw 11, the insertion hole 13d of the callus separation operating jig 13, and the insertion hole 14e of the withdrawal operating jig 14 are not necessary.

REFERENCE SIGNS LIST 2, 2' guide pin
11 medical screw
11a distal end portion
11b screw thread portion
11c drill blade
11d rear end portion
11e head portion
11f rotational operating portion
11g through hole
11h reverse external thread portion
11i groove portion
11j guide portion
12 screwing-in operating jig
13, 13' callus separation operating jig
14 withdrawal operating jig
14a reverse internal thread portion
14b cap nut portion
14c shaft portion
14d grip portion
14e insertion hole

The invention claimed is:

1. A medical screw formed of a metallic material for joining a fracture site comprising:
    a screw thread portion formed on an outer surface of a distal end portion; and
    an external thread portion formed on an outer periphery of a head portion of a rear end portion,
    wherein a top surface of the head portion bulges in an arcuate shape, and
    wherein the external thread portion is screwed with a withdrawal operating jig and formed in a reverse direction to a direction of a thread of the screw thread portion.

2. The medical screw according to claim 1, wherein a through hole for insertion of a guide pin is formed from the distal end portion to the head portion along a center axis.

3. The medical screw according to claim 1, wherein the entire length is 30 to 60 mm.

4. The medical screw according to claim 2, wherein the entire length is 30 to 60 mm.

5. The medical screw according to claim 1, wherein a plurality of groove portions are formed on an outer periphery of the head portion in a direction orthogonal to the circumferential direction.

6. The medical screw according to claim 2, wherein a plurality of groove portions are formed on an outer periphery of the head portion in a direction orthogonal to the circumferential direction.

7. The medical screw according to claim 1, wherein the screw thread portion is a right-handed thread, and the external thread portion is a left-handed thread.

8. The medical screw according to claim 2, wherein the screw thread portion is a right-handed thread, and the external thread portion is a left-handed thread.

* * * * *